(12) United States Patent
Nolan et al.

(10) Patent No.: US 6,316,380 B1
(45) Date of Patent: Nov. 13, 2001

(54) CATALYST SYSTEM COMPRISING TRANSITION METAL AND IMIDAZOLINE-2-YLIDENE OR IMIDAZOLIDINE-2-YLIDENE

(75) Inventors: Steven P. Nolan, New Orleans, LA (US); Jinkun Huang, Des Plaines, IL (US); Mark L. Trudell, Metairie; Chunming Zhang, New Orleans, both of LA (US)

(73) Assignee: University of New Orleans Research & Technology Foundation, New Orleans, LA (US)

( * ) Notice: Subject to any disclaimer, the term of this patent is extended or adjusted under 35 U.S.C. 154(b) by 0 days.

(21) Appl. No.: 09/507,958

(22) Filed: Feb. 22, 2000

Related U.S. Application Data

(60) Provisional application No. 60/154,260, filed on Sep. 16, 1999, provisional application No. 60/121,056, filed on Feb. 22, 1999, and provisional application No. 60/099,722, filed on Sep. 10, 1998.

(51) Int. Cl.$^7$ ........................... B01J 31/00; B01J 27/246; C07D 235/02; C07D 233/54; C07D 233/56
(52) U.S. Cl. ........................... 502/155; 502/162; 502/167; 502/200; 548/303.1; 548/335.1; 548/343.1; 548/345.1; 548/347.1
(58) Field of Search ........................... 502/155, 162, 502/167, 200; 548/303.1, 347.1, 335.1, 343.5, 345.1

(56) References Cited

U.S. PATENT DOCUMENTS

| | | | |
|---|---|---|---|
| 3,992,403 | * 11/1976 | Roebke | 548/347.1 |
| 5,077,414 | * 12/1991 | Arduengo, III | 548/335 |
| 5,104,993 | 4/1992 | Arduengo, III | 548/317 |
| 5,182,405 | * 1/1993 | Arduengo, III | 548/335.1 |
| 5,663,451 | * 9/1997 | Herrmann et al. | 568/451 |
| 5,703,269 | * 12/1997 | Herrmann et al. | 560/19 |
| 5,728,839 | * 3/1998 | Hermann et al. | 548/103 |
| 5,849,929 | * 12/1998 | Volodarsky et al. | 548/347.1 |
| 6,025,496 | * 2/2000 | Herrmann et al. | 548/107 |
| 6,177,575 | * 1/2001 | Arduengo, III et al. | 548/335.1 |

OTHER PUBLICATIONS

Alder, et al., "Stable Carbenes as Strong Bases", J. Chem. Soc., Chem. Commun, 1995, pp. 1267–1268. Apr. 1995.
Arduengo, III et al., "A Stable Crystalline Carbene", J. Am. Chem. Soc., 1991, vol. 113, No. 1, pp. 361–363. Month N/A.
Arduengo, III et al., "An Air Stable Carbene and MIxed Carbene "Dimers"", J. Am. Chem. Soc., 1997, vol. 119, No. 52, pp. 12742–12749. Sep. 1997.
Arduengo, III et al., "Low–Coordiante Carbene Complexes of NIckel(0)", J. Am. Chem. Soc., 1994, vol. 116, No. 10, pp. 4391–4394. Month N/A.
Schönherr, et al., "1.3.4.5–Tetraphenyl–imidazoliumperchlorat", Liebigs Ann. Chem. Bd. 731, 1970, pp. 176–179 (not translated). Month N/A.

Wanzlick et al., "Direct Synthesis of a Mercury Salt–Carbene Complex", Angew Chem, Internat. Edit, 1968, vol. 7, No. 2, pp. 141–142. Nov. 1967.
Chemical Abstracts, vol. 55, Column 21100, Wanzlick et al., "New Contribution to Carbene Chemistry", Angew Chem. vol. 72, p. 494, 1960, Month N/A.
Arduengo, III, et al., "Electronic Stabilization of Nucleophilic Carbenes", J. Am. Chem. Soc., 1992, vol. 114, No. 14, pp. 5540–5534. Jan. 1992.*
Arduengo, III, et al., "A Stable Diaminocarbene", J. Am.Chem. Soc.1995, vol. 117, No. 44, pp. 11027–11028. Aug. 1995.*
Herrmann, et al., "Metal Complexes of N–Hetercyclic Carbenes—A New Structural Principle for Catalysts in Homogeneous Catalysts", Angew Chem. Int. Ed. Engl., 1995, vol. 34, No. 21, pp. 2371–2374. Month N/A.*
Herrmann, et al., "N–Heterocyclic Carbenes[+]: Generation Under Mild Conditions and Formation of Group 8–10 Transition Metal Complexes Relevant to Catalysis", Chem. Eur. J. 1996, vol. 2, No. 7, pp. 772–780. Month N/A.*
Herrmann et al., "N–Heterocyclic Carbenes", Angew. Chem. Int. Ed. Engl., 1997, vol. 36, pp. 2162–2187. Month N/A.*
Huang Jinkum et al., "Olefin Metathesis–Active Ruthenium Complexes Bearing a Nucleophilic Carbene Ligand", J. Am. Chem. Soc., 1999, vol. 121, No. 12, pp. 2674–2678. Sep. 1998.*
Littke, et al., "A Convenient and General Method for Pd–Catalyzed Suzuki Cross–Coupling of Aryl Chlorides and Arylboronic Acids", Angew. Chem. Int. Ed., 1998, vol. 37, No. 24,pp. 3387–3388. Month N/A.*
McGuinness, et al., "Synthesis and Reaction Chemistry of Mixed Ligand Methylpalladium–Carbene Complexes", J. Organometallic Chem., vol. 565, pp. 165–178. Dec. 1997.*
Old, et al., "A Highly Active Catalyst for Palladium–Catalyzed Cross–Coupling Reactions: Room–Temperature Suzuki Couplings and Amination of Unactivated Aryl Chlorides", J. Am. Chem. Soc., 1998, vol. 120, No. 37, pp. 9722–9723. Jun. 1998.*

(List continued on next page.)

Primary Examiner—Mark L. Bell
Assistant Examiner—Patricia L. Hailey
(74) Attorney, Agent, or Firm—Sieberth & Patty, L.L.C.

(57) ABSTRACT

This invention provides a catalyst system useful in many coupling reactions, such as Suzuki, Kumada, Heck, and amination reactions. The catalyst system of the present invention makes use of N-heterocyclic carbenes or their protonated salts. The composition of the catalyst system comprises at least one transition metal compound and at least one N-heterocyclic carbene or its protonated salt. This invention further provides novel N-heterocyclic carbenes and their protonated salts. One type of N-heterocyclic carbene used in this invention is an imidazolinc-2-ylidene wherein the 1 and 3 positions are each, independently, substituted by an aromatic group in which each ortho position is, independently, substituted by a secondary or tertiary group which has at least three atoms.

46 Claims, No Drawings

OTHER PUBLICATIONS

Regitz, Manfred, "Nucleophilic Carbenes: An Incredible Renaissance", Angew. Chem. Int. Ed. Engl., 1996, vol. 35, No. 7, pp. 725–728. Month N/A.*

"Group Notation Revised in Periodic Table" Chemical & Engineering News, 1985, vol. 63, pp. 26–27. Feb. 1985.*

Brescia et al., "Stereoselective Phenylation of Allylic Alcohol Derivatives by Palladium–Catalyzed Cross–Coupling with Hypervalent Silicon Complexes", J. Org. Chem., vol. 63, No. 10, 1998, pp. 3156–3157 (Jan. 1998).

Chuit et al., "Reactivity of Penta–and Hexacoordinate Silicon Compounds and Their Role as Reaction Intermediates", Chem. Rev., vol. 93, 1993, pp. 1371–1372 and 1440–1448 (Feb. 1993).

Denmark et al., "Highly Stereospecific, Cross–Coupling Reactions of Alkenylsilacyclobutanes", J. Am. Chem. Soc., vol. 121, No. 24, 1999, pp. 5821–5822 (Mar. 1999).

Denmark, et al., "Synthesis of Unsymmetrical Biaryls from Arylsilacyclobutanes", Organic Letters, vol. 1, No. 9, 1999, pp. 1495–1498 (Sep. 1999).

Diederich et al., editors, Metal–catalyzed Cross–coupling Reactions, Wiley–VCH Publishing, Chapter 10, author Hiyama "Organosilicon Compounds in Cross–coupling Reactions", 1998, pp. 421–453.

Herrmann et al., "Chelating N–heterocyclic Carbene Ligands in Palladium–Catalyzed Heck–Type Reactions", Journal of Organometallic Chem., 1998, vol. 557, pp. 93–96.

Hiyama et al., "Palladium–catalyzed cross–coupling reaction of organometalloids through activation with fluoride ion", Pure and Applied Chem., vol. 66, No. 7, 1994, pp. 1471–1478.

Horn, Keith, "Regio–and Stereochemical Aspects of the Palladium–Catalyzed Reactions of Silanes", Chem. Rev., vol. 95, 1995, pp. 1317–1350 (May 1995).

Huang, et al., "General and Efficient Catalytic Amination of Aryl Chlorides Using a Palladium/Bulky Nucleophilic Carbene System", Org. Lett. 1999, vol. 1, No. 8, pp. 1307–1309 (Aug. 1999).

Huang et al., "Efficient Cross–Coupling of Aryl Chlorides With Aryl Grignard Reagents (Kumada Reactiion) Mediated by a Palladium/Imidazolium Chloride System", J. Am. Chem. Soc., 1999, vol. 121, No. 42, pp. 9889–9890 May 1999.

Mowery et al., "Improvements in Cross Coupling Reactions of Hypervalent Siloxane Derivatives", Organic Letters, vol. 1, No. 13, 1999, pp. 2137–2140. Oct. 1999.

Mowery et al., "Cross–Coupling Reactions of Hypervalent Siloxane Derivatives: An Alternative to Stille and Suzuki Couplings", J. Org. Chem., vol. 64, No. 5, pp. 1684–1688 Dec. 1988.

Mowery et al., "Synthesis of Unsymmetrical Biaryls by Palladium–Catalyzed Cross Coupling Reactions of Arenes with Tetrabutylammonium Triphenyldifluorosilicate, a Hypervalent Silicon Reagent", J. Org. Chem., vol. 64, No. 9, 1999, pp. 3266–3270 (Jan. 1999).

Pilcher et al., "Utilization of Tetrabutylammonium Triphenyldifluorosilicate as a Fluoride Source for Silicon–Carbon Bond Cleavage", J. Org. Chem., vol. 61, No. 20, 1996, pp. 6901–6905 (May 1996).

Wolfe, et al., "A Highly Active Catalyst for the Room–Temperature Amination and Suzuki Coupling of Aryl Chlorides", Angew. Chem. Int. Ed., 1999, vol. 38, No. 16, pp. 2413–2416.

Zhang et al., "Palladium–Imidazol–2–Ylidene Complexes as Catalysts for Facile and Efficient Suzuki Cross–Coupling Reactions of Aryl Chlorides with Arylboronic Acids", J. Org. Chem., 1999, vol. 64, No. 11, pp. 3804–3805 (Mar. 1999).

* cited by examiner

CATALYST SYSTEM COMPRISING TRANSITION METAL AND IMIDAZOLINE-2-YLIDENE OR IMIDAZOLIDINE-2-YLIDENE

REFERENCE TO RELATED APPLICATIONS

This Application claims the priority date of U.S. Provisional Application No. 60/121,056, filed Feb. 22, 1999, and of U.S. Provisional Application No. 60/154,260 filed Sep. 16, 1999. U.S. Provisional Applications No. 60/121,056 and 60/154,260 incorporate by reference U.S. Provisional Application No. 60/099,722, filed Sep. 10, 1998.

Copending Applications No. 09/507,959, filed Feb. 22, 2000, by us; copending Application No. 09/511,420, filed Feb. 22, 2000, by us; copending Application No. 09/511,122, filed Feb. 22, 2000, by us; and copending Application No. 09/511,654, filed Feb. 22, 2000, by us; may possibly be considered related to the present application.

This invention was made with Government support by the National Institute on Drug Abuse/National Science Foundation under Contract No. RO1 DA11528/9631611. The Government has certain rights in this invention.

The present invention relates to novel catalysts which can be used for chemical synthesis in the polymer and the fine chemical industry, and to novel and eminently useful N-heterocyclic carbenes used in forming such catalysts.

BACKGROUND

Metal catalyzed coupling reactions of aryl bromides, aryl iodides, and aryl pseudohalides (e.g., triflates) with various substrates is a general method employed for the formation of C—C and C—N bonds. Prior art methods generally cannot employ aryl chlorides as feedstock for these chemical transformations, and require the use of more expensive aryl bromides and aryl iodides. The use of aryl chlorides as chemical feedstock in coupling chemistry has proven difficult but would economically benefit a number of industrial processes. The few prior art methods that can employ aryl chlorides use expensive, air-sensitive phosphine ligands. See in this connection Old et al., *J. Am. Chem. Soc.*, 1998, 120, 9722–9723, and Littke and Fu, *Angew. Chem. Int. Ed. Engl.*, 1998, 37, 3387–3388, which describe phosphine-modified, palladium-mediated Suzuki coupling reactions which employ aryl chlorides as substrates. The use of a bulky phosphine (e.g. tri(tert-butyl)phosphine) or phosphine-containing moiety (e.g., di(cyclohexyl)phosphino) in ancillary ligation was shown to be fundamental in triggering the observed catalytic behavior. In addition, these phosphine ligands are often difficult to remove from the process product.

Nucleophilic N-heterocyclic carbenes, the imidazoline-2-ylidenes (sometimes commonly called imidazol-2-ylidenes) or so-called "phosphine mimics", have attracted considerable attention as possible alternatives for the widely used phosphine ligands in homogeneous catalysis. A primary advantage of these ligands is that an excess of the ligand is not required. It appears that these ligands do not dissociate from the metal center, thus preventing aggregation of the catalyst to yield the bulk metal. Further, these imidazoline-2-ylidene carbenes also appear to be more thermally stable than phosphines.

THE INVENTION

This invention provides a catalyst system useful in many coupling reactions, such as Suzuki, Stille, Kumada, and amination reactions. A feature of this invention is the use of an imidazoline-2-ylidene, an imidazolidine-2-ylidene, a bis(imidazoline-2-ylidene), and/or a bis(imidazolidine-2-ylidene) as part of the catalyst system. These N-heterocyclic carbenes and their corresponding salts are inexpensive and readily synthesized.

A first embodiment of this invention is a composition which comprises at least one metal compound comprising at least one transition metal atom and at least one N-heterocyclic carbene or protonated salt of an N-heterocyclic carbene. The N-heterocyclic carbene is selected from the group consisting of i) an imidazoline-2-ylidene wherein the 1 and 3 positions are each, independently, substituted by an aromatic group in which each ortho position is, independently, substituted by a secondary or tertiary group which has at least three atoms, or a protonated salt of such an imidazoline-2-ylidene; ii) an imidazolidine-2-ylidene wherein the 1 and 3 positions are each, independently, substituted by an aromatic group in which each ortho position is, independently, substituted by a secondary or tertiary group having at least three atoms, or a protonated salt of such an imidazolidine-2-ylidene; iii) a bis(imidazoline-2-ylidene) wherein a bridging moiety is bound to one nitrogen atom of each ring, wherein the bridge formed by the bridging moiety has at least five atoms, and wherein the remaining two nitrogen atoms are each, independently, substituted by a secondary or tertiary group which has at least three atoms, or a protonated salt of such a bis(imidazoline-2-ylidene); iv) a bis(imidazolidine-2-ylidene) wherein a bridging moiety is bound to one nitrogen atom of each ring, wherein the bridge formed by the bridging moiety has at least five atoms, and wherein the remaining two nitrogen atoms are each, independently, substituted by a secondary or tertiary group which has at least three atoms, or a protonated salt of such a bis(imidazolidine-2-ylidene); and mixtures of two or more of the foregoing.

Another embodiment of this invention is a novel and highly efficacious group of N-heterocyclic carbenes which have the property or characteristic of greatly enhancing the effectiveness of the foregoing catalyst systems. The N-heterocyclic carbene is selected from the group consisting of i) an imidazoline-2-ylidene wherein the 1 and 3 positions are each, independently, substituted by an aromatic group in which each ortho position is, independently, substituted by a secondary or tertiary group which has at least three atoms, or a protonated salt of such an imidazoline-2-ylidene; ii) an imidazolidine-2-ylidene wherein the 1 and 3 positions are each, independently, substituted by an aromatic group in which each ortho position is, independently, substituted by a secondary or tertiary group having at least three atoms, or a protonated salt of such an imidazolidine-2-ylidene; iii) a bis(imidazoline-2-ylidene) wherein a bridging moiety is bound to one nitrogen atom of each ring, wherein the bridge formed by the bridging moiety has at least five atoms, and wherein the remaining two nitrogen atoms are each, independently, substituted by a secondary or tertiary group which has at least three atoms, or a protonated salt of such a bis(imidazoline-2-ylidene); iv) a bis(imidazolidine-2-ylidene) wherein a bridging moiety is bound to one nitrogen atom of each ring, wherein the bridge formed by the bridging moiety has at least five atoms, and wherein the remaining two nitrogen atoms are each, independently, substituted by a secondary or tertiary group which has at least three atoms, or a protonated salt of such a bis(imidazolidine-2-ylidene); and mixtures of two or more of the foregoing.

Significantly better yields are obtained, often in shorter reaction times, with catalyst systems comprising the N-heterocyclic carbenes of this invention than with catalyst systems which utilize N-heterocyclic carbenes that do not have such limitations.

Further embodiments and features of this invention will be apparent from the ensuing description and appended claims.

The transition metal of the metal compound may be any of those in Groups 4–11 of the Periodic Table. For labeling of the groups of the Periodic Table, see for example, the Periodic Table appearing in *Chemical & Engineering News*, 1985, 69, 26. The metal compound can be in the form of an inorganic salt or an organic metal compound. Inorganic salts that can be used include the bromides, chlorides, fluorides, iodides, cyanides, nitrates, sulfides, sulfites, and sulfates. Organic metal compounds that may be used include complexes and salts such as the carboxylates, e.g., the acetates or propionates, etc. Preferred are metals from Groups 8–11, especially ruthenium, osmium, rhodium, nickel, palladium, platinum, and copper. More preferred transition metals are the Group 10 metals, particularly nickel and palladium, and especially compounds in which the formal oxidation state of nickel or palladium is zero or two. Examples of ruthenium compounds are dichloro(1,5-cyclooctadiene)ruthenium, ruthenium acetate, ruthenium iodide, and the like. Osmium compounds that can be used include osmium chloride. Suitable rhodium compounds include bis(1,5-cyclooctadiene)rhodium trifluoromethanesulfonate and rhodium chloride. Suitable copper compounds include, but are not limited to, copper chloride, copper bromide, and copper cyanide. Suitable nickel compounds include bis(1, 5-cyclooctadiene)nickel, nickel acetate, nickel oxalate, nickel phosphate, nickel stearate, nickel acetylacetonate, nickel tetrafluoroborate, nickel thiocyanate, nickel carbonate, and nickel sulfamate. Examples of palladium compounds include Pd(OAc)$_2$, palladium(II) chloride, Pd(CH$_3$CN)$_4$(BF$_4$)$_2$, PdCl$_2$(CH$_3$CN)$_2$, PdCl$_2$(PhCN)$_2$, PdCl$_2$(PPh$_3$)$_2$, tris(dibenzylideneacetone)dipalladium(0) [which is also referred to herein as dipalladium tris (dibenzylideneacetone)], and palladium trifluoroacetate. Platinum compounds that can be used include platinum acetylacetonate and platinum chloride. More preferred are compounds of palladium. Palladium compounds such as palladium acetate and tris(dibenzylideneacetone) dipalladium(0) are most preferred.

For the imidazoline-2-ylidenes, imidazolidine-2-ylidenes, and their protonated salts, the aryl moiety of the aromatic group at the 1 and 3 positions can be, but is not limited to, phenyl, biphenylyl, naphthyl, and anthracenyl. When the aryl moiety is not a phenyl group, the requirement for ortho substitution is fulfilled, for example, by a 1,3-disubstituted 2-naphthyl moiety (where the naphthyl group is bound to the nitrogen atom at the 2 position of the naphthyl group). Preferred as the aryl moiety is a phenyl group.

The secondary or tertiary group having at least three atoms at the ortho positions can be, for example, isopropyl, cyclopropyl, sec-butyl, tert-butyl, cyclobutyl, 3-pentyl, cyclopentyl, cyclohexyl, 2,5-dimethylhex-2-yl, norbornyl, and adamantyl. Preferably, the secondary or tertiary group has from three to about twelve carbon atoms, and more preferably has from three to about eight carbon atoms. Preferred groups are isopropyl and tert-butyl, especially isopropyl; preferably, both ortho groups are the same. Thus, preferred aromatic groups are 2,6-diisopropylphenyl, 2,6-di (tert-butyl)phenyl, and 2,4,6-triisopropylphenyl.

Examples of imidazoline-2-ylidenes include 1,3-bis(2,6-diisopropylphenyl)imidazoline, 1,3-bis(2-isopropyl-6-tert-butylphenyl)imidazoline, 1,3-bis( 2,6-ditert-butylphenyl) imidazoline, 1,3-bis(2,6-di(cyclohexyl)phenyl)imidazoline, 1,3-bis(2,4,6-triisopropylphenyl)imidazoline, 1,3-bis(2,6-dicyclopropylphenyl)imidazoline, 1,3-bis(2-isopropyl-6-cyclohexyl)phenyl)imidazoline, 1,3-bis(2,6-ditert-butyl-4-methylphenyl)imidazoline, 1,3-bis(2,6-di(sec-butyl)phenyl) imidazoline, 1,3-bis(2,6-di-3-pentylphenyl)imidazoline, 1,3-bis(3-pentyl-6-cyclobutyl)phenyl)imidazoline, 1,3-bis (2,6-di(2,5-dimethylhex-2-yl)phenyl)imidazoline, and the like.

A highly preferred N-heterocyclic carbene is a protonated salt of an imidazoline-2-ylidene of the formula

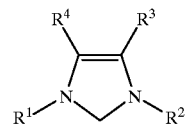

wherein R$^1$ and R$^2$ are 2,6-diisopropylphenyl groups or 2,4,6-triisopropylphenyl groups, and R$^3$ and R$^4$ are each, independently, a hydrogen atom, a halogen atom, or a hydrocarbyl group. Most preferably, R$^3$ and R$^4$ are both hydrogen atoms.

For the bis(imidazoline-2-ylidene)s, bis(imidazolidine-2-ylidene)s and their protonated salts, the bridging moiety can be selected from a large variety of moieties, including alkyl groups, aryl groups, and silyl groups, so long as the bridge has at least five atoms. Preferably, the bridge has five to about eight atoms. Atoms that can form the bridge include, but are not limited to, carbon, nitrogen, oxygen, silicon, and sulfur.

Examples of suitable bridging moieties include 1,5-pentylene, 1,6-hexylene, 1,5-hexylene, benzo (C$_6$H$_4$<), substituted benzo, biphenylene, substituted biphenylene, binaphthylene, and substituted binaphthylene. Heterocyclic aromatic moieties such as, for example, pyridine, pyrimidine, pyrazine, pyridazine, furan, thiophene, oxathiolane, thianthrene, isobenzofuran, phenoxathiin, isothiazole, phenoxazine, and the like, can also form the bridge. The bridging moiety preferably is hydrocarbylene. Preferably, the bridging moiety has from about eight to about thirty carbon atoms, and more preferably has from about ten to about twenty-five carbon atoms. Preferred bridging moieties include biphenylene, binaphthylene, and substituted benzo, with substituted benzo being more preferred. Highly preferred is benzo substituted with methyl groups.

The two nitrogen atoms that are not bound to the bridging moiety are each, independently, substituted by a secondary or tertiary group which has at least three atoms, preferably sterically bulky groups. Suitable groups include, but are not limited to, isopropyl, cyclopropyl, sec-butyl, tert-butyl, cyclobutyl, 3-pentyl, cyclopentyl, cyclohexyl, norbonyl, 2,5-dimethylhex-2-yl, adamantyl, tolyl, 3,5-dimethylphenyl, 2,4,6-trimethylphenyl, 2,6-diisopropylphenyl, 2,4,6-triisopropylphenyl, and 2,4,6-triisopropylphenylmethyl. Preferably, the secondary or tertiary group has from three to about twelve carbon atoms, and more preferably has from three to about eight carbon atoms. Preferably, both secondary or tertiary groups are the same. Preferred groups are tert-butyl, 2,4,6-trimethylphenyl, 2,6-ditert-butylphenyl, 2,6-diisopropylphenyl, and 2,4,6-triisopropylphenyl. The 2,4,6-trimethylphenyl group is most preferred as the secondary or tertiary group for both of the nitrogen atoms that are not bound to the bridging moiety.

Examples of bis(imidazoline-2-ylidene)s include 3,3'-bis [3-(2,4,6-trimethylphenyl)imidazoline-2-ylidene]biphenyl and 2,7-bis[3-(2,6-diisopropylphenyl)imidazoline-2-ylidene]naphthalene.

A highly preferred N-heterocyclic carbene is a protonated salt of a bis(imidazoline-2-ylidene) of the formula

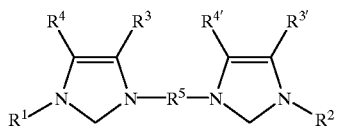

where $R^1$ and $R^2$ are 2,4,6-trimethylphenyl groups, $R^3$, $R^4$, $R^{3'}$, $R^{4'}$ are hydrogen atoms, and $R^5$ is a biphenylene, binaphthylene, or substituted benzo moiety, and the bridge formed by the moiety has at least five atoms.

Particularly preferred protonated salts of bis(imidazoline-2-ylidene)s include

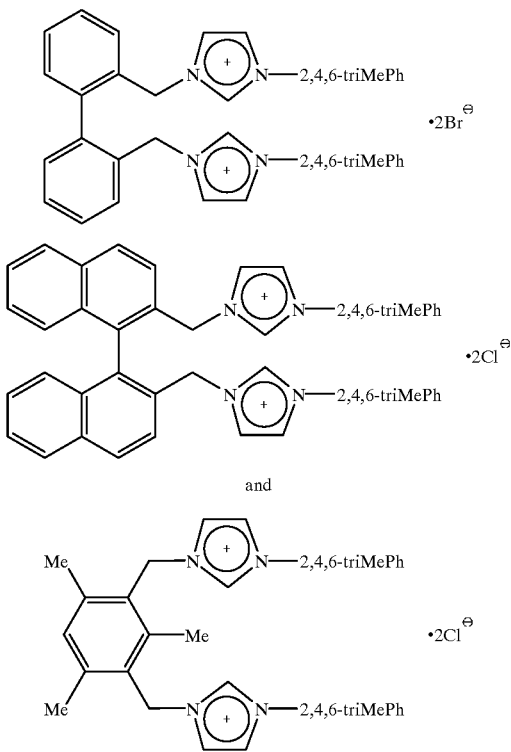

Without being bound by theory, it appears from thermochemical studies that the electron-donating ability of many of the imidazoline-2-ylidene carbene ligands is better than that of tri(cyclohexyl)phosphine and the steric demand of these carbene ligands is greater than that of tri(cyclohexyl) phosphine. This suggests that the N-heterocyclic carbene should possess steric bulk sufficient to stabilize both the free carbene and to stabilize reaction intermediates.

Imidazoline-2-ylidene carbenes and imidazolidine-2-ylidene carbenes are considerably less stable to air and moisture than their corresponding protonated imidazolinium and imidazolidinium salts. Thus, a highly preferred embodiment of this invention involves use of the corresponding imidazolinium salt to generate the imidazoline-2-ylidene in situ (similarly so for the imidazolidine-2-ylidene and the corresponding imidazolidinium salt) to form the catalyst system; this removes the need to handle the N-heterocyclic carbene ligands in an inert atmosphere. Protonated salts of the imidazoline-2-ylidene carbenes and imidazolidine-2-ylidene carbenes are monoprotonated, while the protonated salts of the bis(imidazoline-2-ylidene)s and the bis(imidazolidine-2-ylidene)s are diprotonated. Suitable counterions for the protonated salts are virtually limitless, but halides are preferred counterions. The most preferred counterions are chloride and bromide. The imidazolinium salts are straightforward to synthesize and are air-stable. While the absence of oxygen is not necessary when using a protonated salt of an imidazoline-2-ylidene carbene or an imidazolidine-2-ylidene carbene, it is preferred. When using a neutral carbene, the absence of oxygen is necessary. In any instance where oxygen is excluded, the presence of an inert gas such as nitrogen, helium, or argon is preferred.

Often, a base is included when a protonated salt of an N-heterocyclic carbene is used. A large variety of strong bases are suitable for use in this invention with the protonated carbene salts. Generally, these are inorganic bases. Alkali metal salts are a preferred group of inorganic bases. Examples of suitable alkali metal salts include, but are not limited to, lithium carbonate, lithium tert-butoxide, sodium bicarbonate, sodium carbonate, sodium tert-butoxide, sodium oxide, sodium tetrafluoroborate, potassium acetate, potassium carbonate, potassium fluoride, potassium tert-butoxide, potassium nitrite, potassium phosphate, potassium sulfite, potassium hexafluorophosphate, cesium acetate, cesium bicarbonate, cesium carbonate, cesium fluoride, cesium nitrate, and cesium sulfate. Alkali metal salts of carboxylic acid anions (e.g., acetate, trifluoroacetate, citrate, formate, oxalate, propionate, tartrate, etc.) are also suitable for use as the inorganic base in this invention. More preferred are salts of potassium and cesium. Choice(s) of inorganic base will vary with the particular catalyst system involved. Amine bases have been observed to poison the catalyst system of the invention in some instances, and thus are not preferred.

While not necessary when using protonated salts of N-heteroyclic carbenes, the absence of oxygen and water is preferred when forming the catalyst systems of this invention. Conversely, the exclusion of oxygen and water is generally necessary when neutral carbenes are used. The presence of an inert gas such as argon or nitrogen is preferred when oxygen and/or water are excluded.

Normally, the molar ratio of metal atoms of the metal compound to N-heterocyclic carbene molecules is in the range of from about 1:0.5 to about 1:5, and more preferably in the range of from about 1:1 to about 1:3. When a base is included with the catalyst system of this invention, the base is preferably used in excess.

The following examples are presented for purposes of illustration, and are not intended to impose limitations on the scope of this invention.

EXAMPLES

General Procedures

Reagents

All aryl chlorides (Aldrich Chemical Company), phenylboronic acid (Aldrich), N-methylamine (Aldrich), phenylmagnesium bromide (1.0 moles per liter in tetrahydrofuran; Aldrich), KOtBu (Aldrich), $CS_2CO_3$ (Aldrich), and $Pd_2$(dibenzylideneacetone)$_3$(Strem Chemical Company) were used as received. 1,4-Dioxane was either distilled from Na/benzophenone ketyl or purchased (anhydrous, Aldrich). Flash chromatography was performed on silica gel 60 (230–400 mesh; Natland International Corporation).

1,3-bis(2,4,6-trimethylphenyl)imidazoline-2-ylidene and 1,3-Bis(2,4,6-trimethylphenyl)imidazolinium chloride were prepared according to reported procedures in U.S. Pat. No.

5,077,414, and/or Arduengo, A. J. III., Dias, H. V. R.; Harlow, R. L. and Kline, M. *J. Am. Chem. Soc.*, 1992, 114, 5530–5534. The synthesis of 1,3-bis(2,6-diisopropylphenyl) imidazolinium chloride was carried out in a similar fashion, except that it was done in two steps rather than in one pot (see Example 1).

Analyses

All reactions were monitored by thin layer chromatography (TLC). $^1$H and $^{13}$C nuclear magnetic resonance (NMR) spectra were recorded on a 300 MHz NMR spectrometer (Varian, Incorporated) or 400 MHz NMR spectrometer (Varian) at ambient temperature in $CDCl_3$ (Cambridge Isotope Laboratories, Incorporated).

Conditions

All reactions were carried out under an atmosphere of argon in oven-dried glassware with magnetic stirring, unless otherwise indicated.

Example 1

2,6-Diisopropylaniline (100 g, 0.56 mol), glyoxal (31.5 mL, 40% in water, 0.28 mol), and absolute ethanol (500 mL) were charged to a round-bottom flask. A few drops of formic acid were added, and the solution immediately changed from colorless to yellow. After a few hours, a yellow precipitate appeared. The reaction mixture was stirred for another two days. The yellow precipitate was collected by filtration and washed with cold methanol. 1,4-Bis(2,6-diisopropylphenyl)diazabutadiene was obtained in the amount of 81.74 g, a yield of 77.5%.

Toluene (500 mL) and 1,4-Bis(2,6-diisopropylphenyl) diazabutadiene (25 g, 66 mol) were added to a reaction vessel, followed by solid paraformaldehyde (2.0 g, 66 mmol). The reaction mixture was heated to 100° C. until most of the paraformaldehyde had dissolved. The mixture was then cooled to 40° C., and HCl (16.5 mL, 4 moles per liter in dioxane, 66 mmol) was added via syringe. The reaction mixture turned brown in color, and a white precipitate appeared after a few hours. The reaction mixture was stirred at room temperature for another 36 hours. The precipitate was then collected by filtration and washed with tetrahydrofuran. The yield of 1,3-bis(2,6-diisopropylphenyl) imidazolinium chloride was 13.1 g, or 47%.

Imidazolidine-2-ylidenes can be prepared by hydrogenation of the corresponding imidazolinium salt, for example, with KH in tetrahydrofuran. See in this connection Arduengo et al., *J. Am. Chem. Soc.*, 1995, 117, 11027.

Example 2

Catalyzed amination reactions were carried out using several different imidazolinium-2-ylidene chlorides. For each run, a Schlenk tube was charged with $Pd_2$(dibenzylideneacetone)$_3$ (10 mg, 0.01 mmol), 1,3-bis (substituted)imidazolinium chloride (0.04 mmol), and a magnetic stirring bar. After a 30 minute catalyst activation period, 1,4-dioxane (3 mL), KOtBu (168 mg, 1.5 mmol), 4-chlorotoluene (1.0 mmol), and N-methylaniline (1.2 mmol) were added in turn to the Schlenk tube. The Schlenk tube was placed in a 100° C. oil bath and the mixture was stirred for 3 hours. The mixture was then allowed to cool to room temperature. The mixture was washed with diethyl ether. The organic layer and the diethyl ether extracts were combined, washed with saturated saline solution, and then dried over $MgSO_4$. The solvent was removed under vacuum and the residue was purified by flash chromatography using hexane or a mixture of hexane and ethyl acetate.

The 1,3-bis(substituted)imidazolinium chloride used in each run are listed in Table 1. All of the yields reported in Table 1 are of the heterocoupling product, and are the average of two runs.

TABLE 1

| Run | 1,3-Bis(substituted)imidazolinium chloride | Isolated yield |
|---|---|---|
| A | None | 0 |
| B | 1,3-Bis(p-tolyl)imidazolinium chloride | <5% |
| C | 1,3-Bis(2,6-dimethylphenyl)imidazolinium chloride | 11% |
| D | 1,3-Bis(2,4,6-trimethylphenyl)imidazolinium chloride | 22% |
| E | 1,3-Bis(2,6-diisopropylphenyl)imidazolinium chloride | 98% |

It can be seen that as the steric bulk of the groups bound to the nitrogen atom increases, so does the yield of the reaction. A significant improvement in yield is observed when the ortho methyl groups (Run D) are replaced by isopropyl groups (Run E).

Example 3

Catalyzed Kumada coupling reactions were carried out in a variety of solvents and/or solvent mixtures. For each run, a Schlenk tube was charged with $Pd_2$(dibenzylideneacetone)$_3$ (10 mg, 0.01 mmol), 1,3-bis (substituted)imidazolinium chloride (0.04 mmol), and a magnetic stirring bar. After a 30 minute catalyst activation period, solvent (5 mL), 4-chlorotoluene (1.0 mmol), and phenylmagnesium bromide (1.2 mmol) were added in turn to the Schlenk tube. The Schlenk tube was placed in an oil bath and the mixture was heated and stirred for a number of hours. The mixture was then allowed to cool to room temperature. The mixture was hydrolyzed either with aqueous HCl (1.0 moles per liter) or $H_4NCl$ solution. The solvent was removed under vacuum and the residue was purified by flash chromatography using hexane or a mixture of hexane and ethyl acetate.

The 1,3-bis(substituted)imidazolinium chloride used in each run are listed in Table 2. All of the yields reported in Table 2 are of the heterocoupling product, and are the average of two runs.

TABLE 2

| Run | 1,3-bis(substituted) imidazolinium chloride | Solvent | T | Reaction time | Isolated yield |
|---|---|---|---|---|---|
| a | 1,3-Bis(2,4,6-trimethylphenyl) imidazolinium chloride | Et$_2$O/THF | 45° C. | 20 hr. | 35% |
| b | 1,3-Bis(2,6-diisopropylphenyl) imidazolinium chloride | Et$_2$O/THF | 45° C. | 20 hr. | 97% |
| c | 1,3-Bis(2,6-diisopropylphenyl) imidazolinium chloride | toluene/THF | 80° C. | 20 hr. | 10% |
| d | 1,3-Bis(2,6-diisopropylphenyl) imidazolinium chloride | THF | 80° C. | 5 hr. | 86% |
| e | None | dioxane/THF | 80° C. | 3 hr. | 0 |
| f | 1,3-Bis(2,4,6-trimethylphenyl) imidazolinium chloride | dioxane/THF | 80° C. | 3 hr. | 41% |
| g | 1,3-Bis(2,6-diisopropylphenyl) imidazolinium chloride | dioxane/THF | 80° C. | 3 hr. | 99% |

Comparison of the results in Table 2 clearly shows that, for each solvent or solvent mixture, significantly better yields are obtained with 1,3-bis(2,6-diisopropylphenyl)

imidazolinium chloride, the N-heterocyclic carbene which has secondary groups at the ortho positions of the aromatic rings of the nitrogen-bound groups.

Example 4

Six bis(imidazolinium) salts (see Table 3) were prepared by heating the dibromide or dichloride of the molecule intended to be the bridging moiety with two equivalents of an 1-aryl-imidazol in xylene. As an example, a mixture of dibromomethane (1.0 mmol) and N-(3,5-dimethylphenyl) imidazoline (2.0 mmol) was heated in xylene (5 mL) at 140° C. for 2 days. This afforded the salt shown in Run B of Table 3 in 70% yield. Alternatively, a mixture of 1,3-di(α-chloromethyl)-2,4,6-trimethylbenzene (1.0 mmol) and N-(2,4,6-trimethylphenyl)imidazoline (2.0 mmol) was heated in xylene (5 mL) at 120° C. for 48 hours and furnished the salt shown in Run F of Table 3 in 85% yield.

Bis(imidazolidine-2-ylidene)s can be prepared by hydrogenation of the corresponding imidazolinium salt, for example, with KH in tetrahydrofuran. See in this connection Arduengo et al., *J. Am. Chem. Soc.*, 1995, 117, 11027.

Example 5

Catalyzed Suzuki coupling reactions were carried out using several different bis(imidazolinium-2-ylidene) salts. The procedure used in all runs of this example are as follows. A Schlenk tube was charged with $Pd(CH_3CO_2)_2$ (5.6 mg, 0.025 mmol), one of the bis(imidazolinium-2-ylidene) salts prepared in Example 4 (0.025 mmol), $CS_2CO_3$ (2.00 equivalents), and a magnetic stirring bar. After a 30 minute catalyst activation period, 1,4-dioxane (3 mL), 4-chlorotoluene (1.0 mmol), and phenylboronic acid (1.5 mmol) were added in turn to the Schlenk tube. The Schlenk tube was placed in a 80° C. oil bath and stirred for a number of hours. The mixture was then allowed to cool to room temperature. The bis(imidazoline-2-ylidene) salt used in each run is listed in Table 3. All of the yields reported in Table 3 are of the heterocoupling product, and are the average of two runs.

TABLE 3

| Run | Bis(imidazolinium) salt | Reaction time | Isolated yield |
|---|---|---|---|
| A | 4-MeOPh—N(+)N—CH$_2$—N(+)N—Ph-4-OMe · 2 Br$^\ominus$ | 24 hr. | trace[a] |
| B | 3,5-DiMePh—N(+)N—CH$_2$—N(+)N—Ph-3,5diMe · 2 Br$^\ominus$ | 24 hr. | <5%[a] |
| C | 2,4,6-TriMePh—N(+)N—CH$_2$—N(+)N—Ph-2,4,6-triMe · 2 Br$^\ominus$ | 6 hr. | 32%[a] |
| D | biphenyl-bis[CH$_2$—N(+)N—2,4,6-triMePh] · 2 Br$^\ominus$ | 4 hr. | 65%[a] |
| E | binaphthyl-bis[CH$_2$—N(+)N—2,4,6-triMePh] · 2 Cl$^\ominus$ | 4 hr. | 87% |

TABLE 3-continued

| Run | Bis(imidazolinium) salt | Reaction time | Isolated yield |
|---|---|---|---|
| F | 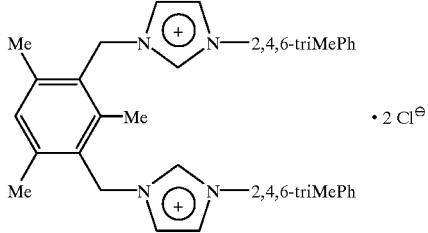 | 1.5 hr. | 99% |

[a] 4-Chlorotoluene was not completely consumed and precipitation of Pd black was observed.

The data in Table 3 clearly demonstrate that dramatically improved yields are obtained in shorter reaction times when the bis(imidazoline-2-ylidene) salt has a bridge of five or more atoms (Runs D–F).

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Whatever transformations, if any, that occur in situ as a reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A composition which comprises
   a) at least one metal compound comprising at least one transition metal atom; and
   b) at least one N-heterocyclic carbene selected from the group consisting of
      i) an imidazoline-2-ylidene wherein the 1 and 3 positions are each, independently, substituted by an aromatic group in which each ortho position is, independently, substituted by a secondary or tertiary group which has at least three atoms, or a protonated salt of such an imidazoline-2-ylidene;
      ii) an imidazolidine-2-ylidene wherein the 1 and 3 positions are each, independently, substituted by an aromatic group in which each ortho position is, independently, substituted by a secondary or tertiary group having at least three atoms, or a protonated salt of such an imidazolidine-2-ylidene;
      iii) a bis(imidazoline-2-ylidene) wherein a bridging moiety is bound to one nitrogen atom of each ring, wherein the bridge formed by the bridging moiety has at least five atoms, and wherein the remaining two nitrogen atoms are each, independently, substituted by a secondary or tertiary group which has at least three atoms, or a protonated salt of such a bis(imidazoline-2-ylidene);
      iv) a bis(imidazolidine-2-ylidene) wherein a bridging moiety is bound to one nitrogen atom of each ring, wherein the bridge formed by the bridging moiety has at least five atoms, and wherein the remaining two nitrogen atoms are each, independently, substituted by a secondary or tertiary group which has at least three atoms, or a protonated salt of such a bis(imidazolidine-2-ylidene);
   and mixtures of two or more of the foregoing.

2. A composition according to claim 1 wherein said transition metal is selected from Groups 8–11 of the Periodic Table.

3. A composition according to claim 1 wherein said transition metal is selected from Group 10 of the Periodic Table.

4. A composition according to claim 1 wherein said metal compound is either a nickel compound or a palladium compound.

5. A composition according to claim 4 wherein the formal oxidation state of the metal is zero or two.

6. A composition according to claim 4 wherein said metal compound is a palladium compound, and is selected from the group consisting of palladium chloride, palladium acetate or dipalladium tris(dibenzylideneacetone).

7. A composition according to claim 4 wherein said metal compound is a nickel compound, and is bis(1,5-cyclooctadiene)nickel.

8. A composition according to claim 1 wherein said N-heterocyclic carbene is selected from the group consisting of an imidazoline-2-ylidene, an imidazolidine-2-ylidene, a protonated salt of an imidazoline-2-ylidene, and a protonated salt of an imidazolidine-2-ylidene.

9. A composition according to claim 8 wherein said secondary or tertiary group at the ortho position of the aromatic group has from three to about twelve carbon atoms.

10. A composition according to claim 8 wherein said aromatic groups are the same, and each is a disubstituted phenyl group.

11. A composition according to claim 10 wherein said disubstituted phenyl group is a 2,6-diisopropylphenyl group.

12. A composition according to claim 11 wherein said metal compound is selected from the group consisting of bis(1,5-cyclooctadiene)nickel, palladium chloride, palladium acetate, and dipalladium tris(dibenzylideneacetone).

13. A composition according to claim 11 wherein said N-heterocyclic carbene is a protonated salt of a imidazoline-2-ylidene.

14. A composition according to claim 1 wherein said N-heterocyclic carbene is selected from the group consisting of a bis(imidazoline-2-ylidene), a bis(imidazolidine-2-ylidene), a protonated salt of a bis(imidazoline-2-ylidene), and a protonated salt of a bis(imidazolidine-2-ylidene).

15. A composition according to claim 14 wherein each said secondary or tertiary group on the remaining two nitrogen atoms has from three to about twelve carbon atoms.

16. A composition according to claim 14 wherein said secondary or tertiary group on the remaining two nitrogen atoms are the same, and each is a substituted phenyl moiety.

17. A composition according to claim 16 wherein said substituted phenyl moiety is selected from the group consisting of a 2,4,6-trimethylphenyl group, a 2,6-diisopropylphenyl group, and a 2,4,6-triisopropylphenyl group.

18. A composition according to claim 14 wherein said bridge has five to about eight atoms.

19. A composition according to claim 14 wherein said bridging moiety has from about eight to about thirty carbon atoms.

20. A composition according to claim 14 wherein the bridging moiety is a biphenylene, binaphthylene, benzo, or substituted benzo moiety.

21. A composition according to claim 17 wherein the bridging moiety is a biphenylene, binaphthylene, benzo, or substituted benzo moiety.

22. A composition according to claim 17 wherein said metal compound is selected from the group consisting of bis(1,5-cyclooctadiene)nickel, palladium chloride, palladium acetate and dipalladium tris(dibenzylideneacetone).

23. A composition according to claim 20 wherein said N-heterocyclic carbene is a protonated salt of a bis(imidazoline-2-ylidene).

24. A composition according to claim 23 wherein said protonated salt of the bis(imidazoline-2-ylidene) is selected from the group consisting of

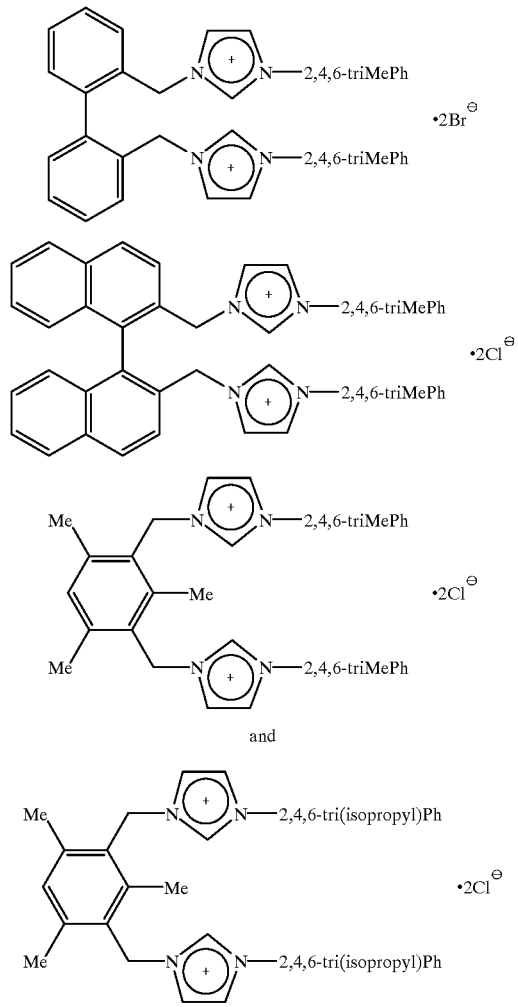

and

25. A composition according to claim 1 wherein a strong base is also included.

26. A composition according to claim 25 wherein said strong base is an alkali metal salt.

27. A composition according to claim 26 wherein said alkali metal salt is selected from the group consisting of potassium carbonate, potassium tert-butoxide, cesium carbonate, and cesium fluoride.

28. A composition which comprises
at least one N-heterocyclic carbene selected from the group consisting of
i) an imidazoline-2-ylidene wherein the 1 and 3 positions are each, independently, substituted by an aromatic group in which each ortho position is, independently, substituted by a secondary or tertiary group which has at least three atoms, or a protonated salt of such an imidazoline-2-ylidene;
ii) an imidazolidine-2-ylidene wherein the 1 and 3 positions are each, independently, substituted by an aromatic group in which each ortho position is, independently, substituted by a secondary or tertiary group having at least three atoms, or a protonated salt of such an imidazolidine-2-ylidene;
iii) a bis(imidazoline-2-ylidene) wherein a bridging moiety is bound to one nitrogen atom of each ring, wherein the bridge formed by the bridging moiety has at least five atoms, and wherein the remaining two nitrogen atoms are each, independently, substituted by a secondary or tertiary group which has at least three atoms, or a protonated salt of such a bis(imidazoline-2-ylidene);

iv) a bis(imidazolidine-2-ylidene) wherein a bridging moiety is bound to one nitrogen atom of each ring, wherein the bridge formed by the bridging moiety has at least five atoms, and wherein the remaining two nitrogen atoms are each, independently, substituted by a secondary or tertiary group which has at least three atoms, or a protonated salt of such a bis(imidazolidine-2-ylidene);

and mixtures of two or more of the foregoing.

29. A composition according to claim 28 wherein said N-heterocyclic carbene is selected from the group consisting of an imidazoline-2-ylidene, an imidazolidine-2-ylidene, a protonated salt of an imidazoline-2-ylidene, and a protonated salt of an imidazolidine-2-ylidene.

30. A composition according to claim 29 wherein said secondary or tertiary group at the ortho position of the aromatic group has from three to about twelve carbon atoms.

31. A composition according to claim 29 wherein said aromatic groups are the same, and each is a disubstituted phenyl group.

32. A composition according to claim 31 wherein said disubstituted phenyl group is a 2,6-diisopropylphenyl group.

33. A composition according to claim 32 wherein said N-heterocyclic carbene is a protonated salt of a imidazoline-2-ylidene.

34. A composition according to claim 28 wherein said N-heterocyclic carbene is selected from the group consisting of a bis(imidazoline-2-ylidene), a bis(imidazolidine-2-ylidene), a protonated salt of a bis(imidazoline-2-ylidene), and a protonated salt of a bis(imidazolidine-2-ylidene).

35. A composition according to claim 34 wherein each said secondary or tertiary group on the remaining two nitrogen atoms has from three to about twelve carbon atoms.

36. A composition according to claim 34 wherein said secondary or tertiary group on the remaining two nitrogen atoms are the same, and each is a substituted phenyl moiety.

37. A composition according to claim 36 wherein said substituted phenyl moiety is either a 2,4,6-trimethylphenyl group or a 2,6-diisopropylphenyl group.

38. A composition according to claim 34 wherein said bridge has five to about eight atoms.

39. A composition according to claim 34 wherein said bridging moiety has from about eight to about thirty carbon atoms.

40. A composition according to claim 34 wherein the bridging moiety is a biphenylene, binaphthylene, benzo, or substituted benzo moiety.

41. A composition according to claim 37 wherein the bridging moiety is a biphenylene, binaphthylene, benzo, or substituted benzo moiety.

42. A composition according to claim 40 wherein said N-heterocyclic carbene is a protonated salt of a bis (imidazoline-2-ylidene).

43. A composition according to claim 42 wherein said protonated salt of the bis(imidazoline-2-ylidene) is selected from the group consisting of

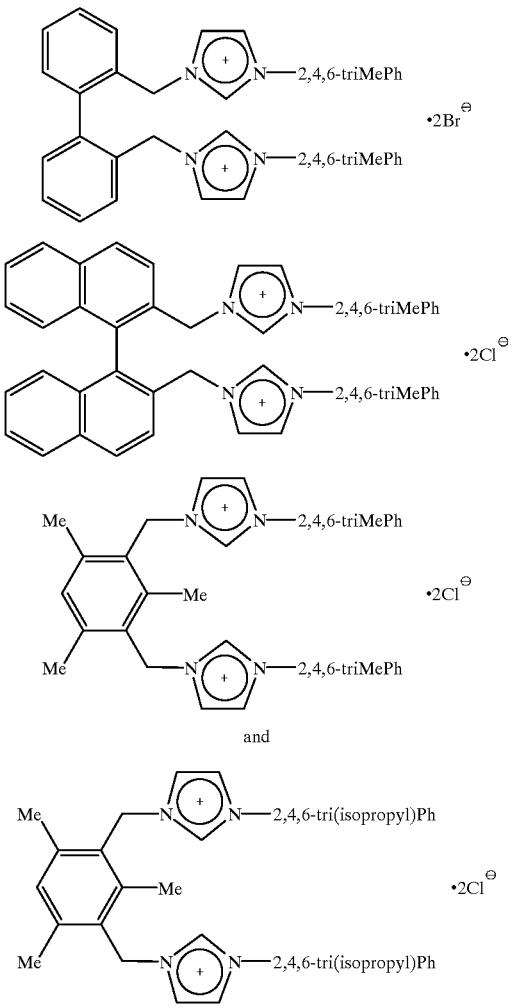

and

44. A composition according to claim 28 wherein a strong base is also included.

45. A composition according to claim 44 wherein said strong base is an alkali metal salt.

46. A composition according to claim 45 wherein said alkali metal salt is selected from the group consisting of potassium carbonate, potassium tert-butoxide, cesium carbonate, and cesium fluoride.

* * * * *

UNITED STATES PATENT AND TRADEMARK OFFICE
CERTIFICATE OF CORRECTION

PATENT NO. : 6,316,380 B1
DATED : November 13, 2001
INVENTOR(S) : Steven P. Nolan et al.

It is certified that error appears in the above-identified patent and that said Letters Patent is hereby corrected as shown below:

<u>Title page,</u>
OTHER PUBLICATIONS, Arduengo, III et al. has "Low-Coordiante Carbene Complexes of NIckel(0)" and should read -- "Low-Coordinate Carbene Complexes of Nickel(0) and Platinum(0)" --.

OTHER PUBLICATIONS, Arduengo, III et al. "Electronic Stabilization......." the page numbers stated are "5540-5534" and should read -- 5530-5534 --.

OTHER PUBLICATIONS, the author name "Huang Jinkum et al.," should read -- Huang, Jinkun et al., --

Signed and Sealed this

Nineteenth Day of March, 2002

Attest:

JAMES E. ROGAN
Attesting Officer   Director of the United States Patent and Trademark Office